(12) United States Patent
Gracey et al.

(10) Patent No.: US 9,199,845 B2
(45) Date of Patent: Dec. 1, 2015

(54) PROCESS FOR PRODUCING ALKENES OXYGENATES BY USING SUPPORTED HETEROPOLYACID CATALYSTS

(75) Inventors: Benjamin Patrick Gracey, Hull (GB); Gordon John Haining, East Riding of Yorkshire (GB); Stephen Roy Partington, Beverley (GB)

(73) Assignee: BP CHEMICALS LIMITED, Middlesex (GB)

( * ) Notice: Subject to any disclaimer, the term of this patent is extended or adjusted under 35 U.S.C. 154(b) by 871 days.

(21) Appl. No.: 12/312,589

(22) PCT Filed: Nov. 8, 2007

(86) PCT No.: PCT/GB2007/004251
§ 371 (c)(1),
(2), (4) Date: May 18, 2009

(87) PCT Pub. No.: WO2008/062157
PCT Pub. Date: May 29, 2008

(65) Prior Publication Data
US 2010/0292520 A1    Nov. 18, 2010

(30) Foreign Application Priority Data

Nov. 22, 2006  (EP) .................................... 06255968
Nov. 22, 2006  (EP) .................................... 06255980

(51) Int. Cl.
*C07C 1/20*    (2006.01)
*C07C 1/24*    (2006.01)
(Continued)

(52) U.S. Cl.
CPC . *C01B 3/32* (2013.01); *B01J 23/30* (2013.01); *B01J 27/188* (2013.01); *B01J 35/002* (2013.01);
(Continued)

(58) Field of Classification Search
CPC .......... B01J 21/06; B01J 27/14; B01J 27/186; B01J 27/188; B01J 27/19

USPC ......... 585/324, 408, 469, 638, 639, 640, 733; 560/247; 518/714; 502/210, 211, 232, 502/254

See application file for complete search history.

(56) References Cited

U.S. PATENT DOCUMENTS 4,396,789 A * 8/1983 Barrocas et al. ............... 585/639
4,687,875 A * 8/1987 Currie et al. ................... 585/469
(Continued)

FOREIGN PATENT DOCUMENTS

EP    0 959 064    11/1999
EP    1 790 627    5/2007
(Continued)

OTHER PUBLICATIONS

Lee et al., Catalysis by Heteropoly Compounds. An NMR Study of Ethanol Dehydration in the Pseudoliquid Phase of 12-Tungstophosphoric Acid; Jl. Am. Chem. Soc., 114, 2836-2842 (1992).*

(Continued)

*Primary Examiner* — In Suk Bullock
*Assistant Examiner* — Philip Louie
(74) *Attorney, Agent, or Firm* — Nixon & Vanderhye P.C.

(57) ABSTRACT

Process for producing alkene(s) from an oxygenate feedstock in a reactor by dehydration in the presence of a supported heteropolyacid catalyst. The pore volume of the supported heteropolyacid catalyst satisfies the following formula:

$$PV>0.6-0.3[HPA \text{loading/Surface Area of Dried Catalyst}] \text{where};$$

PV is the Pore Volume of the dried supported heteropolyacid catalyst (measured in ml/g catalyst); HPA loading is the amount of heteropolyacid present in the dried supported heteropolyacid catalyst (measure in micro moles/g); and Surface Area of Dried Catalyst is the surface area of the dried supported heteropolyacid catalyst (measured in m2/g).

34 Claims, 1 Drawing Sheet

(51) Int. Cl.
*B01J 27/188* (2006.01)
*C01B 3/32* (2006.01)
*B01J 23/30* (2006.01)
*B01J 35/00* (2006.01)
*B01J 35/10* (2006.01)
*B01J 37/02* (2006.01)
*C07C 11/02* (2006.01)
*B01J 21/08* (2006.01)
*B01J 21/12* (2006.01)

(52) U.S. Cl.
CPC .............. *B01J 35/10* (2013.01); *B01J 37/0201* (2013.01); *C07C 1/20* (2013.01); *C07C 11/02* (2013.01); *B01J 21/08* (2013.01); *B01J 21/12* (2013.01); *B01J 35/1019* (2013.01); *B01J 35/1023* (2013.01); *B01J 35/1042* (2013.01); *B01J 35/1047* (2013.01); *B01J 35/1061* (2013.01); *C01B 2203/0227* (2013.01); *C01B 2203/062* (2013.01); *C07C 2521/08* (2013.01); *C07C 2523/30* (2013.01)

(56) References Cited

U.S. PATENT DOCUMENTS

| | | | | |
|---|---|---|---|---|
| 4,752,623 | A * | 6/1988 | Stevens et al. | 518/714 |
| 4,831,060 | A * | 5/1989 | Stevens et al. | 518/714 |
| 5,086,031 | A | 2/1992 | Deller et al. | |
| 5,684,216 | A * | 11/1997 | Haining | 568/896 |
| 5,750,777 | A | 5/1998 | Aubry et al. | |
| 5,861,530 | A | 1/1999 | Atkins et al. | |
| 6,187,949 | B1 * | 2/2001 | Froom et al. | 560/247 |

FOREIGN PATENT DOCUMENTS

| | | |
|---|---|---|
| EP | 1 792 885 | 6/2007 |
| JP | S 56-099426 A | 8/1981 |
| JP | S 56-131527 A | 10/1981 |
| JP | S 57-046925 A | 3/1982 |
| JP | H 08-259494 A | 8/1996 |
| JP | H 09-118647 A | 5/1997 |
| WO | WO 02/20158 | 3/2002 |
| WO | WO 2005/021474 A1 | 3/2005 |
| WO | WO 2006/032843 A1 | 3/2006 |
| WO | WO 2007/003901 A1 | 1/2007 |

OTHER PUBLICATIONS

Haber, et al., "Potassium and Silver Salts of Tungstophosphoric Acid as Catalysts in Dehydration of Ethanol and Hydration of Ethylene" in Journal of Catalysis, 207, 296-306 (2002)—month unknown.*
NIST Data, Ethanol phase change and vapor pressure data, NIST Chemistry Web-Book, available at http://www.webbook.nist.gov—accessed Jan. 19, 2014.*
Matthews, "Green Chemistry" in Kirk-Othmer Encyclopedia of Chemical Technology, 2001, John Wiley & Sons, available on-line Feb. 14, 2003.*
Leofanti, et al., "Surface Area and Pore Texture of Catalysts", Catalysis Today, 41 (1998) 207-219—month unknown.*
Samra, S.E., et al; "Catalytic Properties of Silica-supported 12-Molybdophosphoric Acid in the Conversion of 2-Propanol"; Catalytic Properties of Silica-supported 12-Molybdophosphoric Acid; pp. 191 to 201 (1995).*
Ohtsuka, R., et al; "Studies of the Acidity and Ionic Conductivity of Silica-Supported Heteropoly Compounds. I. The Dehydration of t-Butyl alcohol over Heteropoly Compound Catalysts"; Bull. Chem. Soc. Jpn., vol. 62; 3195-3201, (1989).*
International Search Report for PCT/GB2007/004251, mailed Mar. 14, 2008.
Written Opinion of the International Searching Authority for PCT/GB2007/004251, mailed Mar. 14, 2008.
Benliang, Z., et al; "Production of ethylene via the dehydration of ethanol using a heteropoly acid catalyst"; *Journal of Northeast Normal University*; No. 3; pp. 41-43 (English Translation) 1997.
Benliang, Z., et al; "Production of ethylene via the dehydration of ethanol using a heteropoly acid catalyst"; *Journal of Northeast Normal University*; No. 3; pp. 41-43 (Chinese Language) 1997.
State Intellectual Property Office of People's Republic China; Search Report and Text of the Second Office Action issued in Chinese Application No. 200780050268.4, filed Nov. 8, 2007 (English Translation) 7 pgs.
State Intellectual Property Office of People's Republic China; Search Report and Text of the Second Office Action issued in Chinese Application No. 200780050268.4, filed Nov. 8, 2007 (Chinese Language) 7 pgs.
Popa, Alexandra, et al; "Catalytic Properties of Titania-Supported Heteropoly Acids for Ethanol Oxidation"; *Revue Roumaine de Chimie*; 5193), 211-217 (2006).
Official Action issued in corresponding Japanese Patent Application No. 2009-537689, dated Dec. 13, 2012 with English Translation (6 pgs).

* cited by examiner

PROCESS FOR PRODUCING ALKENES OXYGENATES BY USING SUPPORTED HETEROPOLYACID CATALYSTS

This application is the U.S. national phase of International Application No. PCT/GB2007/004251 filed 8 Nov. 2007, which designated the U.S. and claims priority to Europe Application Nos. 06255968.7 filed 22 Nov. 2006, and 06255980.2, filed 22 Nov. 2006, the entire contents of each of which are hereby incorporated by reference.

The present invention relates to a supported heteropolyacid catalyst and/or its salts and to the production process of the said supported heteropolyacid catalyst and/or its salts.

In particular the present invention provides a use of a supported heteropolyacid catalyst for converting oxygenates to alkenes, whereby an improved process is obtained, in terms of alkene productivity and selectivity, whilst preventing the formation of alkanes.

The present invention further provides an improved process for the production of alkene(s) from an oxygenate feedstock using a supported heteropolyacid catalyst under specific operating conditions.

BACKGROUND OF THE INVENTION

Heteropolyacids are valuable chemical compounds which can be used as acid and/or oxygenate catalysts. The processes cited hereinafter, relate to a variety of examples of various heteropolyacids and/or the method(s) for producing them;

US2006052240 describes a supported catalyst comprising a support having supported thereon at least one member selected from the group consisting of heteropolyacids and heteropolyacid salts, in which the heteropolyacid and/or heteropolyacid salt is substantially present in a surface layer region of the support to a depth of 30% from the support surface.

U.S. Pat. No. 6,624,325 describes a catalyst for producing lower fatty acid esters through esterification of a lower aliphatic carboxylic acid with a lower olefin, comprising a heteropoly acid or a, salt thereof held on a carrier, and having a specific surface area of the catalyst, as measured by a BET method, of 65 m<2>/g-350 m<2>/g. A process for producing the catalyst and a process for producing a lower fatty acid ester by using the catalyst are also provided.

U.S. Pat. No. 5,227,141 describes a membrane catalytic reactor which comprises a heteropolyacid selected from the group consisting of 12-tungstophosphoric acid, 12-molybdophosphoric acid, 12-molybdotungstophosphoric acid, and 12-tungstosilicic acid, and polysulfone membrane is provided. This membrane catalytic reactor is applicable to vapor-phase dehydration, dehydrogenation, oxidation, and simultaneous separation of organic or inorganic materials, particularly vapor-phase dehydration of ethanol.

US2004/024918 describes a catalyst for use in producing a lower aliphatic carboxylic acid ester, wherein the catalyst is produced by a process comprising a step of contacting the catalyst with a gas containing at least one member selected from water, lower aliphatic carboxylic acids and lower aliphatic alcohols; a process for producing the catalyst; and a process for producing a lower aliphatic carboxylic acid ester using the catalyst. The document further describes a siliceous support for use in a catalyst, which has a silicon content of from 39.7 to 46.3% by mass or a silicon content of from 85 to 99% by mass in terms of silicon dioxide or a crush strength of 30 N or more. By the use of a catalyst comprising the support, a lower aliphatic carboxylic acid ester is produced from lower olefin and a lower aliphatic carboxylic acid in a gas phase without causing great reduction of catalytic activity or cracking or abrasion of the catalyst.

Alkene(s) have traditionally been produced by steam or catalytic cracking of hydrocarbons. However, inevitably as oil resources are decreasing, the price of oil is increasing; making light alkene production a costly process. Thus there is an ever-growing need for non-petroleum routes to produce C2 and C2+ alkene(s), particularly ethene and propene, as these make useful starting materials for a number chemical processes, including the production of polymeric compounds, such as, polyethylene and polypropylene.

In recent years the search for alternative starting materials for C2 and C2+ alkene(s), production has led to the use of oxygenates such as alcohols (e.g. methanol, ethanol and higher alcohols). These alcohols provide a particularly attractive route for the production of alkene(s) since the said alcohols may be produced by the fermentation of, for example, sugars and/or cellulosic materials.

Alternatively, alcohols may be produced froth synthesis gas. Synthesis gas refers to a combination of hydrogen and carbon oxides produced in a synthesis gas plant from a carbon source such as natural gas, petroleum liquids, biomass and carbonaceous materials including coal, recycled plastics, municipal wastes, or any organic material. Thus, alcohol and alcohol derivatives may provide non-petroleum based routes for the production of alkene(s) and other related hydrocarbons.

Generally, the production of alcohols, for example methanol, takes place via three process steps: synthesis gas preparation, methanol synthesis, and methanol purification. In the synthesis gas preparation step, an additional stage maybe employed whereby the feedstock is first treated, e.g. the feedstock is purified to remove sulphur and other potential catalyst poisons prior to being converted into synthesis gas. This treatment can also be conducted after syngas preparation; for example, where coal or biomass is employed.

The processes cited hereinafter, relate to examples and alternative processes for the dehydration of an oxygenate feedstock; U.S. Pat. No. 4,543,435 discloses a process for converting an oxygenate feedstock comprising methanol, dimethyl ether or the like in an oxygenate conversion reactor into liquid hydrocarbons comprising C2-C4 alkenes and C5+ hydrocarbons. The C2-C4 alkenes are compressed to recover an ethylene-rich gas. The ethylene-rich gas is recycled to the oxygenate conversion reactor.

U.S. Pat. No. 4,076,761 discloses a process for converting oxygenates to gasoline with the return of a hydrogen-rich gaseous product to a synthesis gas plant or the oxygenate conversion reaction zone.

U.S. Pat. No. 5,177,114 discloses a process for the conversion of natural gas to gasoline grade liquid hydrocarbons and/or alkenes by converting the natural gas to a synthesis gas, and converting the synthesis gas to crude methanol and/or dimethyl ether and further converting the crude methanol/dimethyl ether to gasoline and alkenes. International Patent Application No. 93/13013 to Kvisle et al. relates to an improved method for producing a silicon-alumino-phosphate catalyst which is more stable to deactivation by coking. The patent discloses that after a period of time, all such catalysts used to convert methanol to olefin(s) (MTO) lose the active ability to convert methanol to hydrocarbons primarily because the microporous crystal structure is coked; that is, filled up with low volatility carbonaceous compounds which block the pore structure. The carbonaceous compounds can be removed by conventional methods such as combustion in air.

EPO publication No. 0 407 038A1 describes a method for producing dialkyl ethers comprising feeding a stream containing an alkyl alcohol to a distillation column reactor into a feed zone, contacting the stream with a fixed bed solid acidic catalytic distillation structure to form the corresponding dialkyl ether and water, and concurrently fractionating the ether product from the water and unreacted materials.

U.S. Pat. No. 5,817,906 describes a process for producing light alkenes from a crude oxygenate feedstock comprising alcohol and water. The process employs two reaction stages. Firstly, the alcohol is converted using reaction with distillation to an ether. The ether is then subsequently passed to an oxygenate conversion zone containing a metal aluminosilicate catalyst to produce a light olefin stream.

However, a major disadvantage associated with the typical dehydration methods used for producing alkene(s) from oxygenates, is that aromatic and alkane by-products are usually co-produced together with the targeted alkene products, and prove both difficult and expensive to separate, e.g. to recover ethane from ethane is both complex and expensive. For example, the well known methanol to olefin(s)—MTO—process can be described as the dehydrative coupling of methanol to alkenes and is a well known chemistry that can be employed to produce alkenes from alcohol(s). This mechanism is thought to proceed via a coupling of C1 fragments generated by the acid catalysed dehydration of methanol, possibly via a methyloxonium intermediate. Again, the main disadvantage of the said MTO process is that a range of alkenes are co-produced together with a range of various aromatic and alkane by-products, which in turn makes it very difficult and expensive to recover the desired alkenes.

Molecular sieves such as the microporous crystalline zeolite and non-zeolitic catalysts, particularly silicoaluminophosphates (SAPO), are known to promote the conversion of oxygenates by methanol to olefin (MTO) chemistry to hydrocarbon mixtures. Numerous patents describe this process for various types of these catalysts: U.S. Pat. Nos. 3,928,483, 4,025,575, 4,252,479 (Chang et al.); U.S. Pat No. 4,496,786 (Santilli et al.); U.S. Pat No. 4,547,616 (Avidan at al.); U.S. Pat No. 4,677,243 (Kaiser); U.S. Pat. No. 4,843,183 (Inui); U.S. Pat. No. 4,499,314 (Seddon et al.); U.S. Pat No. 4,447,669 (Harmon et al.); U.S. Pat No. 5,095,163 (Barger); U.S. Pat No. 5,191,141 (Barger); U.S. Pat No. 5,126,308 (Barger); U.S. Pat No. 4,973,792 (Lewis); and U.S. Pat No. 4,861,938 (Lewis).

Additionally, this reaction has a high activation energy step—possibly in the methanol or dimethylether production step—hence to achieve high conversion there is a need for high temperatures, e.g. 450° C., to drive the reactions forward. Conventionally, various means, such as, a heated catalyst recycle and/or "Downtherm" heating systems, have been implemented in such systems in order to obtain such high temperature conditions. Unfortunately operating at these said high temperatures leads to major problems, such as, catalyst deactivation, coking and by-product formation. In order to avoid these problems the reactions may be operated at lower temperatures, but this necessitates an expensive recycle of intermediates and reactants.

These and other disadvantages of the prior art show that there is a clear need, within the field, for an improved and/or alternative process for the production of C2 and C2+ alkene(s) from oxygenates.

SUMMARY OF THE INVENTION

Hence, the present invention specifically sets to overcome these and other disadvantages and relates to a selected group of supported heteropolyacid catalyst and/or its salts, which has specific properties that allow it to have improved qualities when used in processes, such as, the dehydration of oxygenates to alkene(s), the preparation of the said selected group of supported heteropolyacid catalyst and/or it's salts, an improved process, in terms of selectivity, productivity and reduced alkane make, for the dehydration of an oxygenate feedstock in order to produce alkene(s), and to the use of a selected group of supported heteropolyacid catalyst and/or its salts in a process for the dehydration of oxygenates to alkene(s) for improving the alkene(s) selectivity and productivity and reducing the alkane make.

Thus, the present invention provides a supported heteropolyacid catalyst wherein the supported heteropolyacid catalyst is characterised in that the pore volume of the supported heteropolyacid catalyst suffices the following formula:

$$PV > 0.6 - 0.3 [HPA \text{ loading/Surface Area of Dried Catalyst}]$$

and the heteropolyacid loading, per surface area of the supported heteropolyacid catalyst is preferably more than 0.1 (micro moles/m2).

The present invention also provides the use of a supported heteropolyacid catalyst in the process of producing alkene(s) from an oxygenate feedstock, for increasing the selectivity and productivity of alkenes and reducing the formation of alkanes, wherein the supported heteropolyacid catalyst is characterised in that the pore volume of the supported heteropolyacid catalyst suffices the following formula:

$$PV > 0.6 - 0.3 [HPA \text{ loading/Surface Area of Dried Catalyst}]$$

The present invention further provides a process for the production of alkene(s) from an oxygenate feedstock in a reactor, characterised by performing the process at a temperature preferably comprised between 180 and 250° C., in the presence of a supported heteropolyacid catalyst; wherein the supported heteropolyacid catalyst is characterised in that the pore volume of the supported heteropolyacid catalyst suffices the following formula:

$$PV > 0.6 - 0.3 [HPA \text{ loading/Surface Area of Dried Catalyst}]$$

Where for the purposes of the present invention and appending claims:

PV is the Pore Volume of the Dried supported heteropolyacid Catalyst (measured in ml/g catalyst);

HPA loading is the amount of heteropolyacid present in the Dried supported heteropolyacid Catalyst (measured in micro moles/g);

Surface Area of Dried Catalyst is the surface area of the Dried supported heteropolyacid Catalyst (measured in m2/g).

The applicants believe that the production of the alkene(s) from the oxygenate feedstock, as stated by the present invention, is believed to proceed via a combination of two different dehydration mechanisms. The first being the direct dehydration of the oxygenates to the corresponding alkene(s) and water (as shown by Equation 1);

Equation 1

And the second being a two step mechanism, where the oxygenate feedstock is dehydrated via the production of an ether intermediate (as illustrated by Equations 2 and 3);

$$2\,ROH \rightleftharpoons ROR + H_2O \quad \text{Equation 2}$$

Equation 3 where R is an ethyl, propyl, butyl or pentyl group and R' is either hydrogen or a methyl, ethyl or propyl group. Preferably R is either a ethyl or propyl group and R' is either hydrogen or methyl moiety.

Equation 1, shows the endothermic direct elimination of alcohol to alkene(s) and water. Competing with Equation 1, are Equations 2 and 3; the exothermic etherification reaction (Equation 2), and the endothermic elimination of ether(s) to produce alkene(s) and alcohol (Equation 3). However, the overall dehydration of alcohols to alkene(s) is said to be an endothermic process.

According to the present invention and appending claims, all of the main reactions that are occurring (i.e. those reactions that are illustrated above) during the said dehydration process, are catalysed by the use of a supported heteropolyacid catalyst.

The term "heteropolyacid", as used herein and throughout the description of the present invention, is deemed to include inter alia; alkali, alkali earth, ammonium, free acids, bulky cation salts, and/or metal salts (where the salts may be either full or partial salts) of heteropolyacids. Hence, the heteropolyacids used in the present invention are complex, high molecular weight anions comprising oxygen-linked polyvalent metal atoms.

Typically, each anion comprises 12-18, oxygen-linked polyvalent metal atoms. The polyvalent metal atoms, known as the peripheral atoms, surround one or more of the central atoms in a symmetrical manner. The peripheral atoms may be one or more of molybdenum, tungsten, vanadium, niobium, tantalum, or any other polyvalent metal. The central atoms are preferably silicon or phosphorus, but may alternatively comprise any one of a large variety of atoms from Groups I-VIII in the Periodic Table of elements. These include copper, beryllium, zinc, cobalt, nickel, boron, aluminium, gallium, iron, cerium, arsenic, antimony, bismuth, chromium, rhodium, silicon, germanium, tin, titanium, zirconium, vanadium, sulphur, tellurium, manganese nickel, platinum, thorium, hafnium, cerium, arsenic, vanadium, antimony ions, tellurium and iodine. Suitable heteropolyacids include Keggin, Wells-Dawson and Anderson-Evans-Perloff heteropolyacids. Specific examples of suitable heteropolyacids are as follows:

| 12-tungstophosphoric acid | H3[PW12O40]•xH2O |
| 12-molybdophosphoric acid | H3[PMo12O40]•xH2O |
| 12-tungstosilicic acid | H4[SiW12O40]•xH2O |
| 12-molybdosilicic acid | H4[SiMo12O40]•xH2O |
| Cesium hydrogen tungstosilicate | Cs3H[SiW12O40]•xH2O | and the free acid or partial salts of the following heteropolyacids:

| Monopotassium tungstophosphate | KH5[P2W18O62]•xH2O |
| Monosodimn 12-tungstosilicic acid | NaK3[SiW12O40]•xH2O |
| Potassium tungstophosphate | K6[P2W18O62]•xH2O |
| Sodium molybdophosphate | Na3[PMo12O40]•xH2O |
| Ammonium molybdodiphosphate | (NH4)6[P2Mo18O62]•xH2O |
| Potassium molybdodivanado phosphate | K5[PMoV2O40]•xH2O |

Preferred examples of selected improved heteropolyacids are as follows:

| 18-tungstophosphoric acid | H6[P2W18O62]•xH2O |
| 12-tungstophosphoric acid | H3[PW12O40]•xH2O |
| 12-tungstosilicic acid | H4[SiW12O40]•xH2O |
| Cesium hydrogen tungstosilicate | Cs3H[SiW12O40]•xH2O | and the free acid or partial salts of the following heteropolyacids:

| Monopotassium tungstophosphate | KH5[P2W18O62]•xH2O |
| Monosodium 12-tungstosilicic acid | NaK3[SiW12O40]•xH2O |
| Potassium tungstophosphate | K6[P2W18O62]•xH2O |

In addition mixtures of different heteropolyacids and salts can be employed. The preferred heteropolyacids for use in the process described by the present invention is any one or more heteropolyacid that is based on the Keggin or Wells-Dawson structures; more preferably the chosen heteropolyacid for use in the process described by the present invention is any one or more of the following: silicotungstic acid, phosphotungstic acid, silicomolybdic acid and phosphomolybdic acid; and more preferably the chosen heteropolyacid for use in the process described by the present invention is any one or more silicotungstic acid; and most preferably the chosen heteropolyacid for use in the process described by the present invention is 12-tungstosilicic acid ($H_4[SiW_{12}O_{40}].xH_2O$)

Preferably, the heteropolyacids employed according to the present invention have molecular weights of more than 700 and less than 8500, preferably more than 2800 and less than 6000. Such heteropolyacids also include dimeric complexes.

The supported heteropolyacid catalyst may be conveniently prepared by dissolving the chosen heteropolyacid in a suitable solvent, where suitable solvents include polar solvents such as water, ethers, alcohols, carboxylic acids, ketones and aldehydes and/or mixtures thereof and distilled water and/or ethanol are the most preferred solvents. The resulting acidic solution has a heteropolyacid concentration that is preferably comprised between 10 to 80 wt %, more preferably 20 to 70 wt % and most preferably 30 to 60 wt %. This said solution is then added to the chosen support (or alternatively the support is immersed in the solution). The actual volume of acidic solution added to the support is not restricted, and hence may be enough to achieve incipient wetness or wet impregnation, where wet impregnation (i.e. preparation using an excess acidic solution volume relative to, pore volume of support), is the preferred method for the purposes of the present invention.

The resulting supported heteropolyacid may be modified, and various salts of heteropolyacid may then be formed in the aqueous solution either prior to, or during impregnation of the acidic solution onto the support, by subjecting the supported heteropolyacid to a prolonged contact with a solution of a suitable metallic salt or by addition of phosphoric acid and/or other mineral acids.

When using a soluble metallic salt to modify the support, the salt is taken in the desired concentration, with the heteropolyacid solution. The support is then left to soak in the said acidic solution for a suitable duration (e.g. a few hours), with periodic stirring or shaking, after which time it is filtered, using suitable means, in order to remove any excess acid.

When the salt is insoluble it is preferred to impregnate the catalyst with the heteropolyacid and then to tritrate with the salt precursor. This method can improve the dispersion of the heteropolyacid salt. Other techniques such as vacuum impregnation may also be employed.

The impregnated support may then be washed and dried. This may be achieved using any conventional separation technique, including, for example, decantation and/or filtration. Once recovered, the impregnated support may be dried, preferably by placing the impregnated support in an oven at elevated temperature. Typically this drying is conducted at 130 C with a nitrogen flow for 16 hours and then cooled to room temperature. For the purpose of the present description and appended claims, the term "Dried Catalyst" is defined as the catalyst prepared by the preceeding description. Alternatively, or additionally, a dessicator may be employed. On a commercial scale this drying stage is often achieved by a purge of hot inert gas such as nitrogen.

The amount of heteropolyacid impregnated onto the resulting support is suitably in the range of 10 wt % to 80 wt % and preferably in between 20 wt % to 50 wt %, based on the total weight of the heteropolyacid and of the support.

The weight of the catalyst on drying and the weight of the support used, may be used to obtain the weight of the acid on the support by deducting the latter from the former, giving the catalyst loading as a 'g heteropolyacid/kg catalyst' term. The catalyst loading in 'g heteropolyacid/litre support' can also be calculated by using the known or measured bulk density, of the support. The preferred catalytic loading of heteropolyacid is 150 to 600 g heteropolyacid/kg catalyst According to a preferred embodiment of the present invention the average heteropolyacid loading per surface area of the dried supported heteropolyacid catalyst is more than 0.1 micro moles/m2.

It should be noted that the polyvalent oxidation states and hydration states of the heteropolyacids stated previously, and as represented in the typical formulae of some specific compounds (shown above), only apply to the fresh acid before it is impregnated onto the support, and especially before it is subjected to the dehydration process conditions of the present invention. The degree of hydration of the heteropolyacid may affect the acidity of the supported catalyst and hence its activity and selectivity. Thus, either or both of these actions of impregnation and dehydration process may change the hydration and oxidation state of the metals in the heteropolyacids, i.e. the actual catalytic species used, under the process conditions given, may not yield the hydration/oxidation states of the metals in the heteropolyacids used to impregnate the support. Naturally therefore it is only to be expected that such hydration and oxidation states may also be different in the spent catalysts after the dehydration process of the present invention.

According to a preferred embodiment of the present invention, the amount of chloride present in/on the said heteropolyacid supported catalyst is less than 40 ppm, preferably less than 25 ppm and most preferably less than 20 ppm.

Suitable catalyst supports may be in a powder form or alternatively may be in a granular form, or in a pelletised form, a spherical form or as a extrudates (including shaped particles) and include, but are not limited to, Mordenites e.g. montmorillonite, clays, bentonite, diatomous earth, titania, activated carbon, alumina, silica-alumina, silica-titania cogels, silica-zirconia cogels, carbon coated alumina, zeolites, zinc oxide, flame pyrolysed oxides. Supports can be mixed oxides, neutral or weakly basic oxides. Silica supports are preferred, such as silica gel supports and supports produced by the flame hydrolysis of $SiCl_4$. Preferred supports are substantially free of extraneous metals or elements which might adversely affect the catalytic activity of the system. Thus, suitable silica supports are at least 99% w/w pure. Impurities amount to less than 1% w/w, preferably less than 0.60% w/w and most preferably less than 0.30% w/w. The pore volume of the support is preferably more than 0.50 ml/g and preferably more than 0.8 ml/g.

Suitable silica supports include, but are not limited to any of the following: Grace Davison Davicat® Grade 57, Grace Davison Davicat® 1252, Grace Davison Davicat® SI 1254, Fuji Silysia CariAct® Q15, Fuji Silysia CariAct® Q10, Degussa Aerolyst® 3045 and Degussa Aerolyst® 3043. The average diameter of the support particles is 2 to 10 mm, preferably 3 to 6 mm. However, these particles may be crushed and sieved to smaller sizes for example, 0.5-2 mm, if desired.

The average pore radius (prior to impregnation with the heteropolyacid) of the support is 10 to 500 Å, preferably 30 to 175 Å, more preferably 50 to 150 Å and most preferably 60 to 120 Å. The BET surface area is preferably between 50 and 600 m2/g and is most preferably between 150 and 400 m2/g. The support has an average single particle crush strength of at least 1 kg force, suitably at least 2 kg force, preferably at least 6 kg force and more preferably at least 7 kg force. The bulk density of the support is at least 380 g/l, preferably at least 395 g/l.

The single particle crush strength was determined by using a Mecmesin force gauge which measures the minimum force necessary to crush a particle between parallel plates. The crush strength is based on the average of that determined for a set of at least 25 catalyst particles.

The BET surface area, pore volume, pore size distribution and average pore radius were determined from the nitrogen adsorption isotherm determined at 77K using a Micromeritics TRISTAR 3000 static volumetric adsorption analyser. The procedure used was an application of British Standard methods BS4359:Part 1:1984 'Recommendations for gas adsorption (BET) methods' and BS7591:Part 2:1992, 'Porosity and pore size distribution of materials'—Method of evaluation by gas adsorption. The resulting data were reduced using the BET method (over the pressure range 0.05-0.20 P/Po) and the Barrett, Joyner & Halenda (BJH) method (for pore diameters of 20-1000 Å) to yield the surface area and pore size distribution respectively.

Suitable references for the above data reduction methods are Brunauer, S, Emmett, P H, & Teller, E, J. Amer. Chem. Soc. 60, 309, (1938) and Barrett, E P, Joyner, L G & Halenda P P, J. Am. Chem. Soc., 1951 73 373-380.

For the purpose of the above analytical measurements, samples of the supports and "Dried Catalysts" were out gassed for 16 hours at 120° C. under a vacuum of 5×10-3 Torr.

A further embodiment of the said invention is where the chosen catalyst support is first treated with a fluorinating agent; the applicants believe that by fulfilling this said embodiment the catalyst will become more inert and/or acidic thus improving the selectivity and/or effectiveness of the catalyst during the aforementioned dehydration process.

According to the present invention, the feedstock that is used as the starting material for the dehydration reaction (as described hereinabove), is an "oxygenate feedstock" and preferably may comprise either of pure alcohol(s), or pure ether(s) or mixtures thereof.

Preferably the alcohol(s) present in the said oxygenate feedstock are least one monohydric aliphatic alcohols and have one or more alpha hydrogen(s) present, e.g. ethanol, n-propanol and t-butanol; which is a necessity in order to comply with the proposed mechanism of the invention by which the alkene(s) are produced (see Equations 1 to 3). The preferred monohydric aliphatic alcohol(s) are preferably ethanol and/or propanol, or a mixture thereof, for example, a mixture of ethanol and n-propanol and/or iso-propanol. Ideally the alcohols present in the said oxygenate feedstock comprise a mixture of ethanol and n-propanol in order to be dehydrated into the corresponding "target alkene(s)". The term 'target alkenes', as used in the present description and appending claims hereinabove and hereinafter, is understood to mean the alkenes that are produced according to the process described by the present invention and preferably consist of either ethene or propene or a mixture thereof.

According to a preferred embodiment of the present invention, the oxygenate feedstock to be dehydrated has an iso-propanol content of less than 5 wt %, preferably less than 1 wt %, most preferably less than 0.1 wt % and ideally contains no iso-propanol.

A preferred characterizing feature according to the present invention is that oxygenate feedstock to be dehydrated has a total C3+ alcohols (C3+ alcohols being defined as alcohols having at least 4 carbon atoms e.g. n-butanol, iso-butanol and pentanol) content of less than 5 wt %, preferably less than 1 wt %, most preferably less than 0.1 wt % and ideally contains no C3+ alcohols.

Another preferred embodiment, according to the present invention, is that the alcohols present in the oxygenate feedstock to be dehydrated, have a methanol content of less than 5 wt %, preferably less than 2 wt %, most preferably less than 0.5 wt % and ideally there is no methanol in the oxygenate feedstock. Corresponding advantages may accrue from eliminating methanol, i.e.
  (i) Prevention of dimethyl ether formation—dimethyl ether is hard to separate from propylene and ethylene compared to diethyl ether
  (ii) Prevention of MTO chemistry
  (iii) Prevention of alkylation of alkenes e.g. propylene to butene
  (iv) Prevention of formation of methyl ethyl ether (which is harder to separate from ethylene)
  (v) Less waste
  (vi) Lower toxicity
  (vii) Lower vapour pressure—easier to ship
  (viii) Shipping better C:O ratio in feedstock, i.e. less water production Conventional distillation can be used according to the present invention in order to reduce/eliminate the methanol and C3+ alcohols from the alcohols present in the "oxygenate feedstock" to be dehydrated.

According to a preferred embodiment of the present invention, the ethers that may be used as a mixture with the alcohols present in the said "oxygenate feedstock" to be dehydrated, comprise any one or more of the homo, and mixed, ethers derived from the alcohols ethanol and propanol. For example diethyl ether, n-propyl ether, ethyl n-propyl ether, ethyl iso-propyl ether, n-propyl isopropyl ether and iso-propyl ether.

The applicants have unexpectedly found that by using a mixture of the specified alcohol(s) and ether(s) (in terms of concentrations and components) as the oxygenate feedstock of the present invention, they were not only able to achieve a higher selectivity towards the target alkenes, but they additionally found an overall increase in terms of productivity. Thus the present invention provides an improved process, in terms of reduced alkane make and increased selectivity and productivity of alkene(s), for the dehydration of a specific oxygenate feedstock to alkenes in the presence of a supported heteropolyacid catalyst.

According to a preferred embodiment of the present invention, water is permissible in the oxygenate feedstock to be dehydrated; and the said oxygenate feedstock may comprise up to 50 wt % of water, but preferably the said feedstock comprises less than 25 wt % water, and most preferably the feedstock comprises less than 20 wt % of water. However due to processing costs such as the reactor size, heat of vaporization and heat capacity of water, it is preferred to operate with oxygenate feedstocks containing lower levels of water, for example less than 10 wt %, preferably less than 5 wt %.

As heteropolyacids are the chosen catalysts for the process, the levels of water in contact with the catalyst can affect the catalyst stability and activity. For example heteropolyacids show a diminished catalyst stability at low levels of water (<1 wt %) and a diminished activity at high levels of water (>50 wt %). To one skilled in the art it is apparent that the optimum water level will depend on the interaction of a complex set of variables including, alcohol feed composition, pressure, temperature and nature of the heteropolyacid employed. That said, this process has a good ability to separate water out and hence facilitates the use of bioethanol and other bioalcohol(s).

According to the present invention, the process whereby the oxygenate feedstock is dehydrated is preferably conducted in a dehydration reactor, with a vapour phase dehydration reactor being preferred. The reactor is engineered to cope with the exothermic ether formation and the endothermic dehydration to alkenes. The reaction temperature is preferably maintained within a small temperature range, as a temperature that is too low will reduce the rate of olefin manufacture and can lead to condensation of reactants; and too high a temperature can lead to the olefin being contaminated by unacceptable levels of by-products such as same carbon number alkanes. Preferably the temperature profile of the catalyst bed is less than 30° C., more preferably less than 15° C. and most preferably less than 10° C. For a single bed adiabatic reactor, the overall endothermic reaction if allowed to go to thermodynamic equilibrium could result in a theoretical temperature drop of 180° C. Obviously the problem is one of heat management by reactor design. Suitable reactor designs include those capable of handling heat fluxes such as fixed bed, fluidised bed, multi-tubular and multiple fixed bed reactors with inter-stage heaters. Optionally the heat management can be improved by injecting preheated fresh alcohol feed at several points in the reactor bed, at which point the exothermic etherification reaction can partially counteract the overall endotherm. The feed can also be heated further, to above the reaction temperature, in order to provide an additional source of heat.

According to another preferred embodiment of the present invention the ethanol, propanol, ethers together with the water represent at least 90 wt % of the oxygenate feedstock introduced into the vapour phase dehydration reactor, preferably at least 99 wt % of the oxygenate feedstock introduced into the vapour phase dehydration reactor.

According to a preferred embodiment of the present invention, the operating conditions under which the dehydration process is conducted are such that the dehydration process is always operated in a vapour phase state. It is a preferred embodiment that the dehydration process operating pressure is always at least 0.1 MPa, preferably 0.2 MPa, below the dew point pressure and/or that the dehydration process operating temperature is at least 10° C. above the dew point temperature of the feed entering the vapour phase dehydration reactor and the product composition that is present inside the vapour phase dehydration reactor. The latter being dependent on factors such as the initial feed composition and the degree of conversion within the reactor.

For the purposes of the present invention, the 'dew point temperature' is defined as being a threshold temperature. For example, for a given mixture; at a given pressure, if the system temperature is raised to above the dew point temperature, the mixture will exist as a dry gas. Likewise below the dew point temperature, the mixture will exist, as a vapour containing some liquid. And similarly the 'dew point pressure', is defined as being a threshold pressure. For example, for a given mixture, at a given temperature, if the system pressure is below the dew point pressure, the mixture will exist as a dry gas; above the dew point pressure, the mixture will exist as a vapour containing some liquid.

Thus, in keeping with the present invention, the specific temperature at which the dehydration process according to the present invention is conducted is preferably comprised between 180 and 270° C., more preferably between 190 and 260° C. and most preferably between 200 and 250° C. The applicants have unexpectedly found that by operating at these said temperature ranges (which are particularly low when compared to the typical temperatures employed in the field), they were not only able to benefit from the usual advantages of operating a process of a reduced temperature; but, they also found the process according to the present invention had the added advantage in that they were able to obtain a significantly reduced alkane make, e.g. <1000 ppm of ethane in ethene.

The vapour phase reactor used for dehydrating the oxygenates is preferably operated at a pressure of above 0.1 MPa but less than 4.5 MPa, more preferably at a pressure of above 1.0 MPa but less than 3.5 MPa and most preferably at a pressure of above 1.0 MPa but less than 2.8 MPa.

The preferred reaction conditions used within the vapour phase dehydration reactor, according to the present invention, are such that the dehydration process is always run at moderate conversion of oxygenates to corresponding alkenes.

For the purposes of the present invention and appending claims, moderate conversion of the "oxygenate feedstock" into corresponding alkenes, is defined as being the conversion of alcohols (e.g. ethanol and propanol) and/or their corresponding derived ethers into the corresponding alkenes (e.g C2 and C3 alkenes) and means that 10 to 80%, more preferably 20 to 60%, of the alcohols and/or ethers are "converted" per pass. For a reactor with unreacted material recycle (ether and alcohol) operated in a manner to reach steady state the conversion approximates to:

The number of moles of alkenes produced per pass divided by the total number of moles of alcohol and 2 times the ether in the feed stream containing the recycle and with added fresh feed.

This approximation hold true since the reaction is highly selective to alkenes under the preferred reaction conditions.

The experimental studies have shown that the present invention allows the dehydration of an oxygenate feedstock into the corresponding alkenes to be conducted with a much higher selectivity than has previously been achieved in the field, e.g. current MTO chemistry. This said moderate conversion, low temperature, improved selectivity process benefits from improved economics as well as other advantages.

Also, unlike conventional dehydration processes in the field, the present process described herein has no requirement for a distinct and expensive alkane/alkene separation stage or catalyst regeneration.

The formation of ethers during the vapour phase dehydration process is thermodynamically favourable. This ether formation facilitates the separation of water from the product stream as ethanol, n-propanol and iso-propanol are all fully or significantly water miscible and hence readily form water azeotropes during the dehydration process, which makes the separation of the water (a significant by-product of the reaction) from the product stream a very difficult process. However, the formation of ethers such as diethyl ether and di-n-propyl ether, which both have a limited water miscibility and a very low water content azeotrope, allow the recovery of water by use of a decanter even in the presence of unreacted alcohols.

It should be noted that the operation of the process described by the present invention at medium conversion, with water removal during olefin recovery, has the advantage in that it allows convergence towards the optimum reaction conditions with regards to the water content present in the reactor.

The liquid product stream after olefin removal comprises mostly unreacted alcohols, ethers and water. The applicants have found that it is preferable to recycle the major portion of the alcohols and ethers back to the vapour phase dehydration reactor after water by-product removal. As indicated hereinabove, propanol can exist as two isomers n-propanol and iso-propanol; these isomers can interconvert under the reaction conditions so that the alcohol recycle stream may contain some iso-propanol in addition to unreacted ethanol and n-propanol. This isomerisation can also affect the compounds present in the ether proportion of the preferred recycle stream. The aforementioned ethers that are optionally recycled back into the vapour phase dehydration reactor comprise some ethanol and propanol derived ether(s), such as, diethyl ether, n-propyl ether, ethyl n-propyl ether, ethyl isopropyl ether, n-propyl isopropyl ether and iso-propyl ether, which are produced during the dehydration stage.

According to a preferred embodiment of the present invention, a additional separation stage is implemented into the process, whereby preferably at least 80 wt %; more preferably at least 90 wt %; most preferably at least 99 wt %; even more preferably at least 99.9 wt % of the ether(s) are separated from the alkenes. Thus, at least part, preferably all of the aforementioned ether(s) produced and recovered are then preferably recycled into the vapour phase dehydration reactor.

It is also an embodiment of the present invention that at least part, preferably all of the said ether recycle is pre-mixed with the oxygenate feedstock to be dehydrated, prior to entering the vapour phase dehydration reactor of the present invention.

The present invention also encompasses an embodiment whereby a process is provided for the conversion of hydrocarbon to alkene(s) comprising the consecutive steps of:
  a. converting a hydrocarbon feedstock, in a syngas reactor, into a mixture of carbon oxide(s) and hydrogen,
  b. converting the said mixture of carbon oxide(s) and hydrogen from step a in the presence of a particulate catalyst in a reactor under a temperature comprised between 200 and 400° C. and a pressure of 50 to 200 bar into a feedstock comprising—at least one monohydric aliphatic paraffinic alcohol and/or corresponding ether—having from 2 to 5 carbon atoms, and c. proceeding with the process, as described by the present invention, to produce alkenes; whereby, the oxygenate feedstock comprises at least part of the alcohol(s) and/or ethers produced in step b.

For the purpose of the above embodiment, any hydrocarbon containing feed stream that can be converted into a feedstock comprising carbon monoxide and hydrogen, most preferably a synthesis gas (or "syngas"), is useful in the processes of the invention.

The hydrocarbon feedstock used for syngas generation is preferably a carbonaceous material, for example biomass, plastic, naphtha, refinery bottoms, smelter off gas, municipal waste, coal, coke and/or natural gas, coal and natural gas being the preferred ones, most preferably natural gas.

Feedstocks comprising carbon monoxide and hydrogen, e.g., synthesis gas, may undergo purification prior to being fed to any reaction zones. Synthesis gas purification may be carried out by processes known in the art. See, for example, Weissermel, K. and Arpe H.-J., Industrial Organic Chemistry, Second, Revised and Extended Edition, 1993, pp. 19-21.

BRIEF DESCRIPTION OF THE DRAWINGS

The invention is further described with reference to the accompanying drawings, in which.

EXAMPLES AND COMPARATIVE EXAMPLES

Support Materials Used in the Examples

Silica pellets of CariAct® Q6, CariAct® Q10, CariAct® Q15, CariAct® Q30, CariAct® Q50 were obtained from Fuji Silysia Silica extrudates of Aerolyst® 3043 and Aerolyst® 3045 were obtained as extrudates from Degussa Silica granules of Davicat® Grade 57 and Davicat® 1252 and Davicat® 1254 were obtained from Grace Davison Silica pellets Perlkat® 97-0, Perlkat® 39-3, Perlkat® 25-0 were obtained from Engelhard Silica aluminate pellets T4640 and T4641 were obtained from Sud Chemie Support Properties The support materials were analysed by nitrogen porosimetry (TABLE 1).

TABLE 1

| Support | Surface Area (m2/g) | Pore Volume (cm3/g) | Mean PSD (Å) |
|---|---|---|---|
| Perlkat 97-0 | 343 | 0.81 | 95 |
| Perlkat 39-3 | 743 | 0.64 | 35 |
| Davicat 1252 | 381 | 1.04 | 109 |
| Davicat 1254 | 559 | 0.83 | 59 |
| Aerolyst 3043 | 174 | 0.98 | 226 |
| Aerolyst 3045 | 156 | 0.93 | 239 |
| Sud Chemie T4640 | 156 | 0.37 | 94 |
| Sud Chemie T4641 | 166 | 0.43 | 104 |
| Perlkat 25-0 | 734 | 0.44 | 24 |
| CariAct Q6 | 359 | 0.62 | 69 |
| CariAct Q10 | 303 | 1.06 | 139 |
| CariAct Q15 | 208 | 1.02 | 196 |
| Cariact Q30 | 112 | 0.7 | 250 |
| Cariact Q50 | 71 | 0.69 | 387 |
| Davicat Grade 57 | 284 | 1.11 | 156 |

Catalyst Preparations Using Water as Solvent

Silicotungstic acid (H4[SiW12O40].24H2O, Mw 3310.6) was weighed into a wide-necked plastic bottle and dissolved in distilled water. To this acid solution was added a weighed amount of the support material. The acid solution and support material was left to soak for approximately 1 hr with the occasional gentle swirl during this period to dislodge any trapped air bubbles.

After soaking the unadsorbed acid solution was removed by pouring the acid solution and support material out of the plastic container and into a plastic filter (which contained a filter paper).

The catalyst was allowed to drain until for approximately 15 to 60 minutes until no more liquid was being removed from the catalyst.

After draining was complete the catalyst was transferred to a ceramic tray and dried in a muffle furnace at 130° C. under nitrogen The dried solid catalyst was weighed and the amount of silicotungstic acid adsorbed on the catalyst calculated by difference in weight to the starting material as indicated in the below TABLE 2.

TABLE 2

| Catalyst | Example | Support | Support wt (g) | HPA (g) | Water for HPA solution (g) | Weight catalyst (g) | HPA absorbed (g) | HPA Loading g/kg catalyst |
|---|---|---|---|---|---|---|---|---|
| A | Comparative | Perlkat 25-0 | 30.09 | 15.49 | 47.52 | 34.25 | 4.16 | 121 |
| B |  | Perlkat 97-0 | 30.07 | 24.03 | 59.46 | 38.70 | 8.63 | 223 |
| C | Comparative | Perlkat 39-3 | 30.20 | 27.11 | 53.16 | 35.31 | 5.11 | 145 |
| D |  | Davicat Grade G57 | 30.06 | 32.36 | 76.70 | 40.70 | 10.64 | 261 |
| E |  | Davicat Grade G57 | 30.39 | 64.73 | 65.85 | 52.89 | 22.50 | 425 |
| F |  | Aerolyst 3043 | 30.07 | 29.37 | 68.83 | 41.12 | 11.04 | 269 |
| G |  | Aerolyst 3045 | 30.24 | 28.34 | 64.04 | 40.96 | 10.72 | 262 |
| H |  | CariAct Q10 | 30.51 | 32.28 | 69.79 | 42.21 | 11.70 | 277 |
| I |  | Davicat Grade G57 | 30.17 | 97.08 | 55.52 | 66.76 | 38.59 | 548 |

TABLE 2-continued

| Catalyst | Example | Support | Support wt (g) | HPA (g) | Water for HPA solution (g) | Weight catalyst (g) | HPA absorbed (g) | HPA Loading g/kg catalyst |
|---|---|---|---|---|---|---|---|---|
| J | | CariAct Q30 | 30.08 | 31.77 | 69.45 | 41.50 | 11.42 | 275 |
| K | | CariAct Q50 | 30.10 | 33.80 | 71.12 | 41.50 | 11.40 | 275 |
| L | | Davicat Grade G57 | 30.34 | 19.42 | 77.39 | 37.17 | 6.83 | 184 |
| M | | Davicat 1252 | 30.16 | 31.80 | 70.87 | 41.64 | 11.48 | 276 |
| N | | Davicat 1254 | 30.08 | 27.25 | 58.38 | 36.77 | 6.69 | 182 |
| O | Comparative | T4640 | 30.17 | 31.77 | 54.07 | 37.92 | 7.76 | 205 |
| P | Comparative | T4641 | 30.06 | 33.55 | 57.00 | 38.91 | 8.85 | 228 |
| Q | | CariAct Q15 | 15.04 | 15.61 | 34.56 | 21.16 | 6.12 | 289 |
| R | Comparative | CariAct Q6 | 30.42 | 25.58 | 46.14 | 37.48 | 7.06 | 188 |

Catalyst Preparations Using Ethanol as Solvent

The above procedure was followed except that ethanol was used as the solvent. A small amount of n-butanol was also added to the ethanol (TABLE 3).

TABLE 3

| Catalyst | Example | Support | Support wt (g) | HPA (g) | EtOH & n-BuOH for HPA solution (g) | Weight catalyst g | HPA absorbed (g) | HPA Loading g/kg |
|---|---|---|---|---|---|---|---|---|
| S | | Aerolyst 3043 | 30.59 | 62.87 | 47.969 & 1.499 | 59.63 | 29.04 | 487 |

Catalyst Properties

The dried solid catalysts were analysed by nitrogen porosimetry (TABLE 4).

TABLE 4

| Catalyst | Example | Support | Surface Area of Catalyst (m2/g) | Pore Volume of Catalyst (cm3/g Cat) | Mean PSD of Catalyst (Å) | HPA (g)/ Surface Area of Catalyst (m2) | HPA (µmoles)/ Surface Area of Catalyst (m2) | Calculation of Equation (1) |
|---|---|---|---|---|---|---|---|---|
| A | Comparative | Perlkat 25-0 | 509 | 0.33 | 26 | 0.00024 | 0.07 | 0.5785 |
| B | | Perlkat 97-0 | 246 | 0.58 | 95 | 0.00091 | 0.27 | 0.5178 |
| C | Comparative | Perlkat 39-3 | 518 | 0.49 | 38 | 0.00028 | 0.08 | 0.5746 |
| D | | Grace Davison G57 | 207 | 0.74 | 142 | 0.00126 | 0.38 | 0.4857 |
| E | | Grace Davison G57 | 144 | 0.52 | 144 | 0.00295 | 0.89 | 0.3325 |
| F | | Aerolyst 3043 | 128 | 0.68 | 212 | 0.00210 | 0.63 | 0.4095 |
| G | | Aerolyst 3045 | 120 | 0.63 | 211 | 0.00218 | 0.66 | 0.4021 |
| H | | CariAct Q10 | 242 | 0.69 | 114 | 0.00114 | 0.35 | 0.4963 |
| I | | Grace Davison G57 | 123 | 0.38 | 125 | 0.00446 | 1.35 | 0.1962 |
| J | | CariAct Q30 | 91 | 0.67 | 292 | 0.00302 | 0.91 | 0.3261 |
| K | | CariAct Q50 | 62 | 0.37 | 241 | 0.00444 | 1.34 | 0.1980 |
| L | | Grace Davison G57 | 209 | 0.83 | 159 | 0.00088 | 0.27 | 0.5202 |
| M | | Grace Davison 1252 | 227 | 0.59 | 104 | 0.00122 | 0.37 | 0.4898 |
| N | | Grace Davison 1254 | 374 | 0.59 | 64 | 0.00049 | 0.15 | 0.5559 |
| O | Comparative | T4640 | 90 | 0.27 | 119 | 0.00228 | 0.69 | 0.3936 |
| P | Comparative | T4641 | 118 | 0.3 | 103 | 0.00193 | 0.58 | 0.4249 |
| Q | | CariAct Q15 | 148 | 0.66 | 179 | 0.00195 | 0.59 | 0.4230 |
| R | Comparative | CariAct Q6 | 298 | 0.42 | 57 | 0.00063 | 0.19 | 0.5428 |
| S | | Aerolyst 3043 | 123 | 0.4 | 129 | 0.00398 | 1.20 | 0.2411 |

Equation (1)=0.6−0.3*[HPA Loading(μmoles/g)/Surface Area of Catalyst (m2/g)]

When calculating the micromoles of heteropolyacid (HPA) adsorbed on the catalyst it is assumed that the hetropolyacid is fully hydrated. A Mw of 3310.6 was used for calculating the micro moles of 12-silicotungstic acid (H4[SiW12O40].24H2O) adsorbed Catalyst Testing Catalysts (0.8 to 0.92 ml, 125 to 180 um particle size) were loaded into parallel flow reactors. Weights and volumes of the catalysts were recorded.

TABLE 5

| Catalyst | Example | Support | Weight (g) | Volume (ml) |
| --- | --- | --- | --- | --- |
| A | Comparative | Perlkat 25-0 | 0.6527 | 0.804 |
| B | | Perlkat 97-0 | 0.5365 | 0.859 |
| C | Comparative | Perlkat 39-3 | 0.5001 | 0.901 |
| D | | Davicat G57 | 0.6531 | 0.845 |
| E | | Davicat G57 | 0.6438 | 0.707 |
| F | | Aerolyst 3043 | 0.5365 | 0.914 |
| G | | Aerolyst 3045 | 0.5365 | 0.914 |
| H | | CariAct Q10 | 0.5250 | 0.852 |
| I | | Davicat G57 | 0.7848 | 0.776 |
| J | | CariAct Q30 | 0.5120 | 0.887 |
| K | | CariAct Q50 | 0.5252 | 0.817 |
| L | | Davicat G57 | 0.4532 | 0.831 |
| M | | Davicat 1252 | 0.5439 | 0.776 |
| N | | Davicat 1254 | 0.5713 | 0.790 |

TABLE 5-continued

| Catalyst | Example | Support | Weight (g) | Volume (ml) |
| --- | --- | --- | --- | --- |
| O | Comparative | T4640 | 0.6886 | 0.804 |
| P | Comparative | T4641 | 0.6430 | 0.776 |
| Q | | CariAct Q15 | 0.5810 | 0.859 |
| R | Comparative | CariAct Q6 | 0.7160 | 0.845 |
| S | | Aerolyst 3043 | 0.7623 | 0.804 |

The reactors were pressure tested and then heated to 220° C. under a nitrogen flow. When the temperature had reached 220° C. the liquid feed of ethanol, diethyl ether and water were vapourised and mixed with nitrogen prior to being admitted to the reactor containing the catalyst. The reaction conditions were 20 bar, nominal GHSV of 3000 h-1 for a 1 ml catalyst bed, EtOH (28% v/v), Diethyl ether (34.5% v/v), water (3.3% v/v) and nitrogen (34.2% v/v). When using small volume parallel flow reactors there will always be slight variations in the actual weight and volume of the catalyst(s) loaded into the separate reactor. Any variation in the volume of the catalysts loaded then leads to a variation in the actual GHSV used since each individual reactor has the same total gas flow passing through it The catalysts were tested under the sequence of temperatures; 220° C. for 24 hrs (Phase 1), 210° C. for 24 hrs (Phase 2), 230° C. for 24 hrs (Phase 3), 240° C. for 24 hrs (Phase 4) before finally being tested at 220° C. for 24 hrs again (Phase 5).

TABLE 6

| Catalyst | Example | Support | Reactor Temperature (° C.) | reactor-pressure (bar) | GHSV (h−1) | Phase |
| --- | --- | --- | --- | --- | --- | --- |
| A | Comparative | Perlkat 25-0 | 220 | 20.00 | 3697 | Phase 5 |
| B | | Perlkat 97-0 | 220 | 19.97 | 3460 | Phase 5 |
| C | Comparative | Perlkat 39-3 | 220 | 19.97 | 3298 | Phase 5 |
| D | | Davicat Grade 57 | 220 | 19.98 | 3517 | Phase 5 |
| E | | Davicat Grade 57 | 220 | 20.01 | 4203 | Phase 5 |
| F | | Aerolyst 3043 | 220 | 20.02 | 3252 | Phase 1 |
| G | | Aerolyst 3045 | 220 | 19.97 | 3251 | Phase 5 |
| H | | CariAct Q10 | 220 | 20.20 | 3488 | Phase 5 |
| I | | Davicat Grade 57 | 220 | 20.01 | 3830 | Phase 5 |
| J | | CariAct Q30 | 220 | 19.98 | 3350 | Phase 5 |
| K | | CariAct Q50 | 220 | 20.02 | 3638 | Phase 1 |
| L | | Davicat Grade 57 | 220 | 19.98 | 3577 | Phase 5 |
| M | | Davicat 1252 | 220 | 20.01 | 3830 | Phase 5 |
| N | | Davicat 1254 | 220 | 20.01 | 3762 | Phase 5 |
| O | Comparative | T4640 | 220 | 20.01 | 3696 | Phase 5 |
| P | Comparative | T4641 | 220 | 20.00 | 3829 | Phase 5 |
| Q | | CariAct Q15 | 220 | 20.20 | 3460 | Phase 5 |
| R | Comparative | CariAct Q6 | 220 | 20.20 | 3518 | Phase 5 |
| S | | Aerolyst 3043 | 220 | 20.01 | 3697 | Phase 5 |

The flow rate of the exit gas from the reactors was measured and the exit gas was also analysed by a GC using flame ionisation detectors. Ethylene, ethane, ethanol, diethyl ether, butanes, butanes and acetaldehyde were detected by GC. Product rates were calculated from the gas flow and analysed composition.

The catalysts exhibited the following average catalyst performance, over the phase period defined above, as regards ethylene productivity and ethane selectivity (as defined by ethane/ethylene ratio—(TABLE 7).

TABLE 7

| Catalyst | Example | Support | Pore Volume of Catalyst (cm3/g Cat) | HPA (umoles)/ Surface Area of Catalyst (m2) | Calculation of Equation (1) | HPA g/kg cat | Ethene (g/kg cat/h) | Ethane (g/kg cat/h) | Ethane in Ethylene (ppm) |
|---|---|---|---|---|---|---|---|---|---|
| A | Comparative | Perlkat 25-0 | 0.33 | 0.07 | 0.58 | 121 | 295 | 0.66 | 2249 |
| B | | Perlkat 97-0 | 0.58 | 0.27 | 0.52 | 223 | 1222 | 1.03 | 844 |
| C | Comparative | Perlkat 39-3 | 0.49 | 0.08 | 0.57 | 145 | 59 | 0.17 | 2781 |
| D | | Grace Davison G57 | 0.74 | 0.38 | 0.49 | 261 | 1676 | 0.45 | 267 |
| E | | Grace Davison G57 | 0.52 | 0.89 | 0.33 | 425 | 2095 | 0.53 | 255 |
| F | | Aerolyst 3043 | 0.68 | 0.63 | 0.41 | 262 | 1782 | 0.72 | 406 |
| G | | Aerolyst 3045 | 0.63 | 0.66 | 0.40 | 262 | 1966 | 0.55 | 278 |
| H | | CariAct Q10 | 0.69 | 0.35 | 0.50 | 277 | 1622 | 0.57 | 351 |
| I | | Grace Davison G57 | 0.38 | 1.35 | 0.20 | 548 | 1636 | 0.49 | 297 |
| J | | CariAct Q30 | 0.67 | 0.91 | 0.33 | 275 | 1502 | 0.57 | 382 |
| K | | CariAct Q50 | 0.37 | 1.34 | 0.20 | 275 | 1234 | 1.04 | 836 |
| L | | Grace Davison G57 | 0.83 | 0.27 | 0.52 | 184 | 1343 | 0.54 | 400 |
| M | | Grace Davison 1252 | 0.59 | 0.37 | 0.49 | 276 | 1945 | 0.43 | 224 |
| N | | Grace Davison 1254 | 0.59 | 0.15 | 0.56 | 182 | 1398 | 0.56 | 400 |
| O | Comparative | T4640 | 0.27 | 0.69 | 0.39 | 205 | 461 | 1.13 | 2452 |
| P | Comparative | T4641 | 0.3 | 0.58 | 0.42 | 228 | 743 | 0.87 | 1175 |
| Q | | CariAct Q15 | 0.66 | 0.59 | 0.42 | 289 | 1706 | 0.46 | 269 |
| R | Comparative | CariAct Q6 | 0.422 | 0.19 | 0.54 | 188 | 878 | 1.00 | 1142 |
| S | | Aerolyst 3043 | 0.4 | 1.20 | 0.24 | 487 | 1897 | 0.84 | 443 |

Equation (1) = 0.6 − 0.3 * [HPA Loading (μmoles/g)/Surface Area of Catalyst (m2/g)]

The mass balance was consistently above 95%, the detected by-products are given as ratios to the ethene, the analytical system employed was capable of detecting C1-C6 hydrocarbons and oxygenates. As illustrated above the catalysts according to the present invention are highly selective.

Figure 1:
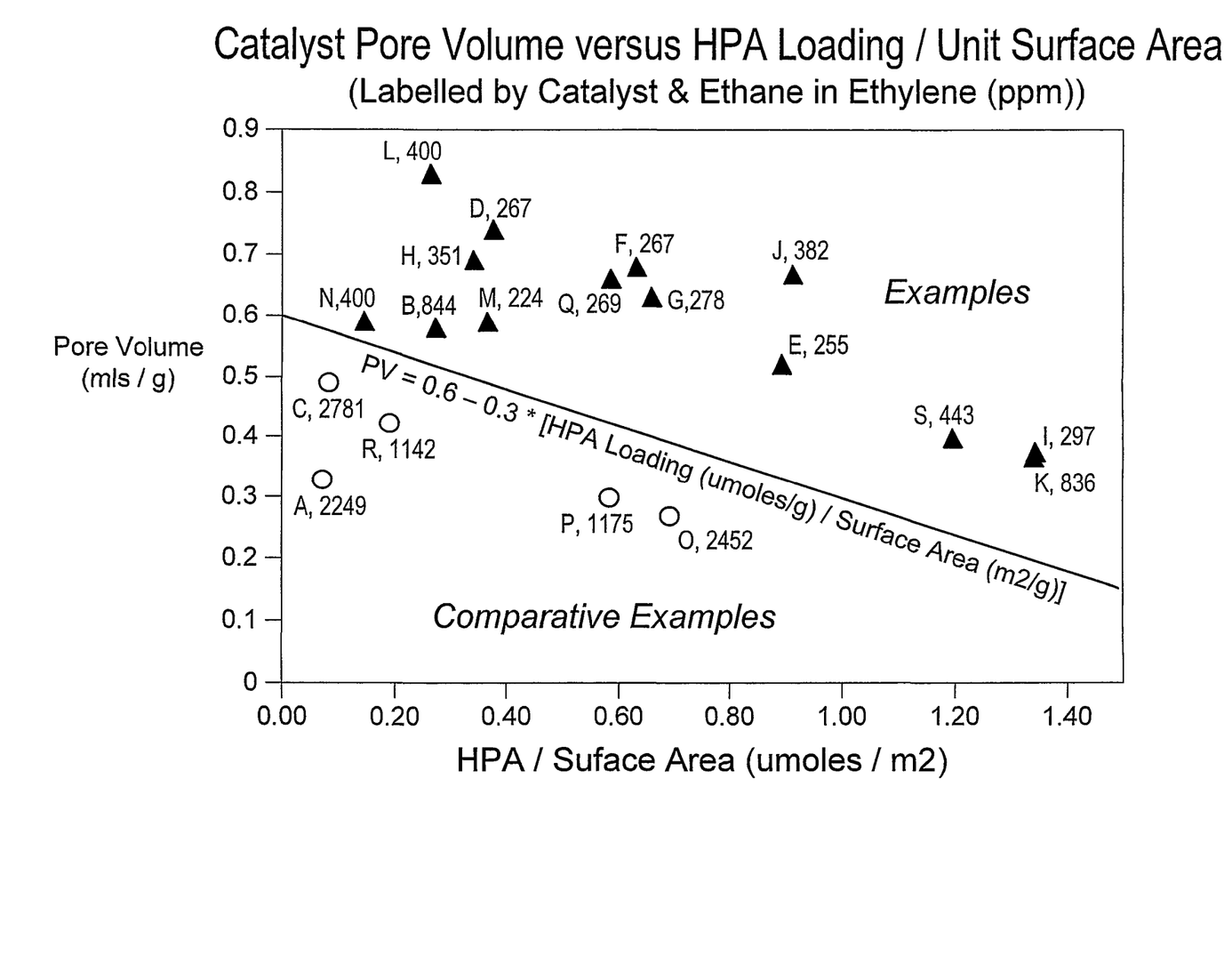
FIG. 1 is a plot of catalyst pore volume versus ratio of HPA loading to surface area of the catalyst.

These examples and comparative examples have been plotted into FIG. 1 which represents the catalyst pore volume (cm3/g) versus the ratio of HPA loading (umoles/g) to surface area (m2/g) of the catalyst. The value of the ethane in ethene (ppm) has been indicated on each example in the FIGURE.

The invention claimed is:

1. A dehydration process for producing alkene(s) from an oxygenate feedstock comprising at least one monohydric aliphatic alcohol having one or more alpha hydrogen(s) and/or corresponding ether, comprising contacting the oxygenate feedstock with a supported heteropolyacid catalyst selected from the group consisting of silicotungstic acid, silicomolybdic acid and phosphomolybdic acid, in a dehydration reactor to produce the alkene(s), wherein the pore volume of the supported heteropolyacid catalyst suffice the following formula:

$$PV > 0.6 - 0.3[HPA\text{loading}/\text{Surface Area of Dried Catalyst}],$$ where:

PV is the Pore Volume of the dried supported heteropolyacid catalyst (measured in ml/g catalyst);

HPA loading is the amount of heteropolyacid present in the dried supported heteropolyacid catalyst (measured in micro moles/g);

Surface Area of Dried Catalyst is the surface area of the dried supported heteropolyacid catalyst (measured in $m^2/g$).

2. A process according to claim 1, wherein the HPA loading per surface area of the supported heteropolyacid catalyst is more than 0.1 micro moles/$m^2$.

3. A process according to claim 1, wherein the supported heteropolyacid catalyst has a catalytic loading of between 150 to 600 g heteropolyacid /kg catalyst.

4. A process according to claim 1, wherein the pore volume of the catalyst support of the supported heteropolyacid catalyst is more than 0.50 ml/g.

5. A process according to claim 1, wherein the catalyst support of the supported heteropolyacid catalyst has an average pore radius of between 10 to 500 Å.

6. A process according to claim 1, wherein the catalyst support of the supported heteropolyacid catalyst has a BET surface area between 50 and 600 $m^2/g$.

7. A process according to claim 1, wherein the catalyst support of the supported heteropolyacid catalyst has an average single particle crush strength of at least 1 kg force.

8. A process according to claim 1, wherein the catalyst support of the supported heteropolyacid catalyst has a bulk density of at least 380 g/l.

9. A process according to claim 1, wherein the catalyst support of the supported heteropolyacid catalyst is a silica support.

10. A process according to claim 1, wherein the dehydration process is operated at a temperature of between 180 and 250° C.

11. A process according to claim 1, wherein the dehydration process is conducted in the vapour phase state.

12. A process according to claim 1, wherein the dehydration process is operated at a pressure of at least 0.1 MPa below the dew point pressure and/or that the dehydration process is operated at a temperature of at least 10 ° C. above the dew point temperature of the feed entering the dehydration reactor and the product composition that is present inside the dehydration reactor.

13. A process according to claim 1, wherein the dehydration process is operated at a temperature of between 180 and 270° C.

14. A process according to claim 1, wherein the dehydration process is operated at a pressure, of above 0.1 MPa but less than 4.5 MPa.

15. A process according to claim 1, wherein the oxygenate feedstock comprises alcohol(s) and the majority of the unreacted alcohols and/or ethers produced during the dehydration process are recycled back to the dehydration reactor.

16. A process according to claim 15, wherein at least part of the said unreacted alcohols and/or ether recycle is pre-mixed with the oxygenate feedstock to be dehydrated prior to entering the dehydration reactor.

17. A process for the conversion of hydrocarbon to alkene(s) comprising the consecutive steps of:
   a) converting a hydrocarbon feedstock, in a syngas reactor, into a mixture of carbon oxide(s) and hydrogen,
   b) converting the said mixture of carbon oxide(s) and hydrogen from step a in the presence of a particulate catalyst in a reactor under a temperature comprised between 200 and 400° C. and a pressure of 50 to 200 bar into a feedstock comprising at least one monohydric aliphatic paraffinic alcohol and/or corresponding ether having from 2 to 5 carbon atoms, and
   c) proceeding with the process as claimed in claim 1 to produce alkenes;
   whereby, the oxygenate feedstock comprises at least part of the alcohol(s) and/or ethers produced in step b.

18. A process according to claim 1, wherein the pore volume of the catalyst support of the supported heteropolyacid catalyst is more than 0.8 ml/g.

19. A process according to claim 1, wherein the catalyst support of the supported heteropolyacid catalyst has an average pore radius of between 30 to 175 Å.

20. A process according to claim 1, wherein the catalyst support of the supported heteropolyacid catalyst has an average pore radius of between 50 to 150 Å.

21. A process according to claim 1, wherein the catalyst support of the supported heteropolyacid catalyst has an average pore radius of between 60 to 120 Å.

22. A process according to claim 1, wherein the catalyst support of the supported heteropolyacid catalyst has a BET surface area between 150 and 400 $m^2/g$.

23. A process according to claim 1, wherein the catalyst support of the supported heteropolyacid catalyst has an average single particle crush strength of at least 2 kg force.

24. A process according to claim 1, wherein the catalyst support of the supported heteropolyacid catalyst has an average single particle crush strength of at least 6 kg force.

25. A process according to claim 1, wherein the catalyst support of the supported heteropolyacid catalyst has an average single particle crush strength of at least 7 kg force.

26. A process according to claim 1, wherein the catalyst support of the supported heteropolyacid catalyst has a bulk density of at least 395 g/l.

27. A process according to claim 1, wherein the dehydration process is operated at a pressure of at least 0.2 MPa below the dew point pressure and/or that the dehydration process is operated at a temperature of at least 10 ° C. above the dew point temperature of the feed entering the dehydration reactor and the product composition that is present inside the dehydration reactor.

28. A process according to claim 1, wherein the dehydration process is operated at a temperature of between 190 and 260° C.

29. A process according to claim 1, wherein the dehydration process is operated at a temperature of between 200 and 250 ° C.

30. A process according to claim 1, wherein the dehydration process is operated at a pressure of above 1.0 MPa but less than 3.5 MPa.

31. A process according to claim 1, wherein the dehydration process is operated at a pressure of above 1.0 MPa but less than 2.8 MPa.

32. A process according to claim 11, wherein the oxygenate feedstock comprises alcohol(s) and the majority of the unreacted alcohols and/or ethers produced during the dehydration process are recycled back to the vapour phase dehydration reactor.

33. A process according to claim 32, wherein at least part of the said unreacted alcohols and/or ether recycle is pre-mixed with the oxygenate feedstock to be dehydrated prior to entering the vapour phase dehydration reactor.

34. A process according to claim 32, wherein all of the said unreacted alcohols and/or ether recycle is pre-mixed with the oxygenate feedstock to be dehydrated prior to entering the vapour phase dehydration reactor.

* * * * *